United States Patent

Pfister et al.

[11] 4,314,950
[45] Feb. 9, 1982

[54] PROCESS FOR THE PREPARATION OF SULPHONIC ACID CHLORIDES

[75] Inventors: Theodor Pfister, Wuppertal; Wolfgang Schenk, Leverkusen; Heinz U. Blank, Odenthal, all of Fed. Rep. of Germany

[73] Assignee: Bayer Aktiengesellschaft, Leverkusen, Fed. Rep. of Germany

[21] Appl. No.: 146,827

[22] Filed: May 5, 1980

Related U.S. Application Data

[63] Continuation of Ser. No. 944,457, Sep. 21, 1978, abandoned.

[30] Foreign Application Priority Data

Sep. 28, 1977 [DE] Fed. Rep. of Germany ....... 2743541

[51] Int. Cl.$^3$ ............................................ C07C 143/26
[52] U.S. Cl. ................................................ 260/543 R
[58] Field of Search .................................... 260/543 R

[56] References Cited

U.S. PATENT DOCUMENTS 3,706,794 12/1972 Horner ........................... 260/543 H
4,105,692 8/1978 Blank et al. ..................... 260/543 R
4,215,071 7/1980 Blank et al. ..................... 260/543 R Primary Examiner—Paul J. Killos
Attorney, Agent, or Firm—Sprung, Felfe, Horn, Lynch & Kramer

[57] ABSTRACT

An improvement in a process for the preparation of a sulphonic acid chloride of the formula

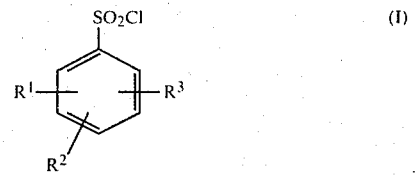

wherein $R^1$, $R^2$ and $R^3$ are independently hydrogen, a lower alkyl radical or a cycloalkyl radical, halogen, aryl, aralkyl, aryl ether or a radical $-SO_2Cl$, $-SO_2$-aryl

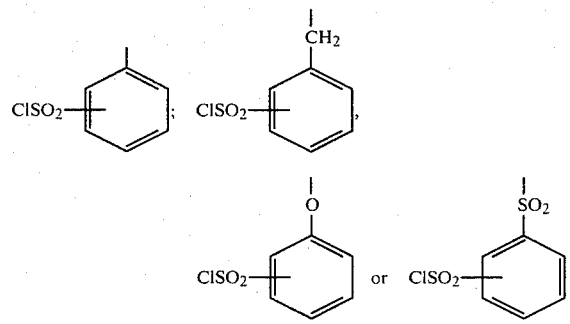

or wherein adjacent radicals $R^1$ and $R^2$ are linked to form a cycloaliphatic, aromatic or hetero-aromatic ring which is optionally substituted by a sulphonic acid chloride group wherein an aromatic compound of the formula

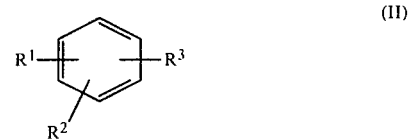

wherein $R^1$, $R^2$ and $R^3$ have the above-identified meanings is reacted initially with chlorosulphonic acid and thereafter the reaction product is reacted with phosgene in the presence of a catalyst.

16 Claims, No Drawings

PROCESS FOR THE PREPARATION OF SULPHONIC ACID CHLORIDES

This is a continuation of application Ser. No. 944,457, filed Sept. 21, 1978, now abandoned.

The invention relates to a process for the preparation of sulphonic acid chlorides by reacting aromatic compounds with chlorosulphonic acid and phosgene.

It is known (Ullmanns Enzyklopädie per technischen Chemie (Ulmann's Encyclopaedia of Industrial Chemistry), 4th edition, volume 8 (1974), page 420) to prepare benzenesulphonyl chloride by reacting benzene with excess chlorosulphonic acid. The use of excess chlorosulphonic acid is a considerable disadvantage of this process, especially with respect to protection of the environment, since the excess chlorosulphonic acid is hydrolysed with water to hydrogen chloride and sulphuric acid during the working up of the reaction mixture and is obtained as so-called dilute acid, together with the sulphuric acid also additionally formed as a by-product and together with considerable amounts of benzenesulphonic acid which have not been converted into the sulphonic acid chloride. The working up and removal of this dilute acid unavoidably obtained leads to considerable expense. In the case of simple neutralisation of the dilute acid, a corresponding salt content in the effluent results, which is also undesirable for reasons of protection of the environment and makes expensive desalination of the effluent necessary.

A process has now been found for the preparation of sulphonic acid chlorides of the formula

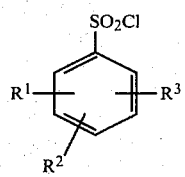
(I)

wherein $R^1$, $R^2$ and $R^3$ are identical or different and denote hydrogen, a lower alkyl radical or a cycloalkyl radical, halogen, aryl, aralkyl, aryl ether or a radical —$SO_2Cl$, —$SO_2$-aryl,

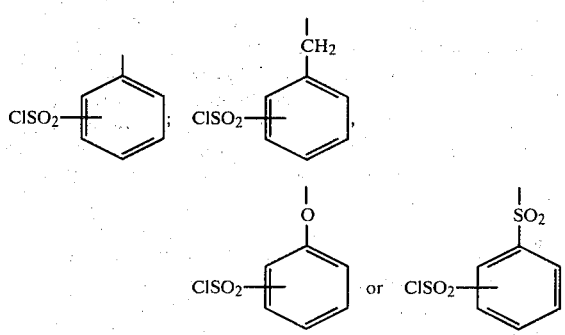

or wherein adjacent radicals $R^1$ and $R^2$ are linked to form a cycloaliphatic, aromatic or hetero-aromatic ring which is optionally substituted by a sulphonic acid chloride group, by reacting an aromatic compound of the formula

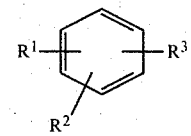
(II)

wherein $R^1$, $R^2$ and $R^3$ have the abovementioned meaning, with chlorosulphonic acid and phosgene, in which approximately stoichiometric amounts of the aromatic compound and chlorosulphonic acid are first reacted, optionally in the presence of a solvent and optionally in the presence of a sulphonation auxiliary, and the product is then reacted with phosgene in the presence of a catalyst.

Lower alkyl radicals ($R^1$ to $R^3$) can be straight-chain or branched alkyl radicals with 1 to 6, preferably 1 to 4, carbon atoms. Examples which may be mentioned are: methyl, ethyl, propyl, isopropyl, butyl, isobutyl, pentyl, hexyl and isohexyl.

Examples of cycloalkyl radicals ($R^1$ to $R^3$) which may be mentioned are cyclopentyl and cyclohexyl, preferably cyclohexyl.

Halogens ($R^1$ to $R^3$) which may be mentioned are fluorine, chlorine, bromine and iodine, preferably fluorine, chlorine and bromine.

Phenyl may be mentioned as an example of the aryl radicals ($R^1$ to $R^3$).

Examples of possible aralkyl radicals ($R^1$ to $R^3$) are those with 6 to 18 carbon atoms, the aliphatic part of which contains 1 to 6 carbon atoms and the aromatic part of which is a radical from the benzene series. The following araliphatic radicals may be mentioned as examples: benzyl, $\beta$-phenyl-ethyl, $\gamma$-phenyl-propyl and $\beta$-phenyl-n-hexyl, preferably benzyl.

An aryl ether radical ($R^1$ to $R^3$) which may be mentioned is, in particular, the phenoxy radical.

Fused ring systems, such as indane, tetralin and naphthalene, preferably naphthalene, are formed by the linking of the adjacent radicals $R^1$ and $R^2$ to give a cycloaliphatic or aromatic ring.

One can, of course, employ for the radicals $R^1$ to $R^3$ further substituted radicals. Examples which may be mentioned include halogen, lower alkyl, aryl, aroxy, alkoxy and aralkyl.

Preferred aromatic compounds which may be mentioned are compounds of the formula

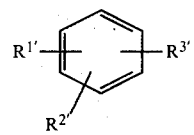
(III)

wherein $R^{1'}$, $R^{2'}$ and $R^{3'}$ are identical or different and denote hydrogen, an alkyl radical with 1 to 4 carbon atoms, fluorine, chlorine, bromine, phenyl, phenoxy, —$SO_2$— phenyl, —$SO_2Cl$ or benzyl, or wherein adjacent radicals $R^{1'}$ and $R^{2'}$ are linked to form a cycloaliphatic, aromatic or hetero-aromatic ring with 5 or 6 ring members.

The following aromatic compounds may be mentioned as examples: benzene, toluene, ethylbenzene, isopropylbenzene (cumene), tetralin, o-xylene, m-xylene, p-xylene, diphenyl, diphenylmethane, chlorobenzene, 1-chloronaphthalene, 2-chloronaphthalene, o-chlorotoluene, 1,2-, 1,3- and 1,4-dichlorobenzene, 2,3-, 2,4-, 2,5-, 3,4- and 2,6-dichloro-toluene, 2,3-2,4-, 2,6-, 3,4- and 2,5-dimethylchlorobenzene, bromobenzene, fluorobenzene, 1,2,3- and 1,2,4-trichlorobenzene, diphenyl ether, naphthalene, 1- and 2-methylnaphthalene and 2-, 3- and 4-bromotoluene, diphenyl sulphone, benzenesulphonyl chloride, toluenesulphonyl chloride, diphenylene sulphone and diphenylene oxide.

Benzene is the particularly preferred starting compound.

The process according to the invention is preferably carried out in the presence of sulphonation auxiliaries. In general, sulphonation auxiliaries in the process according to the invention are compounds which can act as Lewis bases towards chlorosulphonic acid.

Examples of sulphonation auxiliaries which may be mentioned for the process according to the invention are:

1. Carboxylic acids and their derivatives, such as, acetic acid, propionic acid, butyric acid, pivalic acid, valeric acid, caproic acid and adipic acid, halogenated carboxylic acids, such as mono-, di- and tri-chloroacetic acid, carboxylic acid anhydrides, such as, for example, acetic anhydride, propionic anhydride, succinic anhydride and phthalic anhydride, carboxylic acid chlorides, such as, for example, acetyl chloride, propionyl chloride, butyryl chloride and adipyl dichloride, carboxylic acid esters, such as, for example, acetic acid methyl ester and ethyl ester, and carboxylic acid amides, such as, for example, formamide, dimethylformamide, phthalimide and succinimide, 2. urea and alkylureas, 3. Phosphoric acid and organic phosphorus compounds, such as, for example, trimethyl, triethyl and tributyl phosphate and trimethyl and triethyl phosphite, 4. ethers, such as, for example, diethyl ether, tetrahydrofurane and dioxane, 5. ketones, such as, for example, acetone, methyl ethyl ketone, methyl propyl ketone, methyl isobutyl ketone, cyclopentanone and cyclohexanone, and 6. amines, such as, for example, mono-, di- and triethylamine, isopropylamine, tert.-butylamine, cyclohexylamine, ethanolamine, morpholine, pyridine and imidazole.

carboxylic acids and their derivatives and phosphorus compounds are particularly preferred; dimethylformamide, acetic acid and phosphoric acid are especially preferred.

The sulphonation auxiliary can be used in an amount from 0.5 to 10 mol %, preferably from 1 to 8 mol % and especially from 2 to 5 mol %; in general, all or some of it can be initially introduced at the start of the reaction. The portion which has optionally not been added is then added dropwise or in portions during the further course of the first reaction stage.

In the process according to the invention, for example, the chlorosulphonic acid is initially introduced in the first process stage, together with the sulphonation auxiliary, and the aromatic compound is added at a rate depending on the rate of reaction, which can be determined using the evolution of hydrogen chloride.

In general, the chlorosulphonic acid is employed in approximately stoichiometric amounts, relative to the number of sulphonic acid chloride groups to be introduced. However, it can be advantageous to employ a slight excess of up to 20 mol %, and in particular of up to 5 mol %.

In general, the first process step of the process according to the invention is carried out in a temperature range from about 0° to 150° C., preferably from 10° to 140° C. and particularly preferred from 20° to 100° C., in the presence of a sulphonation auxiliary.

The reaction mixtures of the aromatic compounds and chlorosulphonic acid are usually liquid and easily stirrable within the temperature range indicated, even after the reaction. It is therefore indeed possible to use a solvent which is inert towards chlorosulphonic acid, but this is usually not necessary.

Possible solvents or diluents for the process according to the invention are liquid sulphur dioxide, hydrocarbons and halogenohydrocarbons, in particular halogenoalkanes, such as, for example, methylene chloride, chloroform and carbon tetrachloride, di-, tri- and tetra-chloroethylene, di-, tri-, tetra- and penta-chloroethane, 1,1,2-trichloro-1,2,2-trifluoroethane and tetrafluoroethylene.

The first process stage of the process according to the invention is preferably carried out under normal pressure; however, it can also be carried out under reduced pressure or under increased pressure up to 10 bars, in particular up to 5 bars.

If the reaction temperature is higher than the temperature under reflux conditions under normal pressure, the reaction is appropriately carried out under a pressure which corresponds to the vapour pressure of the reaction mixture under the particular conditions chosen.

When the chlorosulphonic acid is initially introduced, up to about 100° C. it is also possible to carry out the reaction under normal pressure by adding the aromatic compound dropwise or by passing in the gaseous aromatic compound.

Unreacted aromatic compound can be recovered virtually quantitatively by distillation.

The second process stage can be carried out directly after the first process stage, usually also without using solvents. Since it is not necessary to isolate the intermediate products, the process according to the invention can be carried out as a "one-pot reaction."

In the second process stage, the phosgene is generally used in excess of the stoichiometrically required amount of 1 mol of phosgene per mol of the aromatic compound. An excess of up to 100 mol %, preferably from 10 to 50 mol %, of phosgene is usually employed. It is, of course, also possible to use larger excesses of phosgene, but in general this brings no advantage. Unreacted, excess phosgene can be recovered and re-used.

The second process stage of the process according to the invention is carried out in the presence of a catalyst. Phosgenation catalysts are in themselves known (U.S. Pat. No. 3,673,247, French Pat. No. 1,513,766, DT-OS (German Published Specification) No. 1,593,906, DT-OS (German Published Specification) No. 1,963,383 and DT-OS (German Published Specification) No. 2,240,883). The following phosgenation catalysts may be mentioned as examples: dimethylformamide, dimethylacetamide, N-methylpyrrolidone, triethylamine, N,N-dimethylaniline, pyridine, triphenylphosphine and triphenylphosphine oxide.

Dimethylformamide is preferably used.

The second process stage of the process according to the invention, that is to say the reaction of phosgene with the reaction mixture from the first process stage, is carried out in a manner such that phosgene is always present in the reaction mixture in excess during the reaction, relative to the sulphonic acid formed in the first process stage.

In general, the reaction with phosgene is carried out in the temperature range from 0° to 100° C., preferably from 20° to 80° C. and in particular from 40° to 70° C. The second process stage is also preferably carried out under normal pressure; however, it can also be carried out under reduced pressure or under increased pressure. If low-boiling solvents or a large excess of phosgene are used, the process is carried out under reflux under a pressure adapted to the required sump temperature.

Phosgene, which is contained in the off-gas of the second reaction stage, can be recovered, for example by washing with dichlorobenzene. However, it can also be advantageous to carry out the off-gas wash additionally or exclusively with sulphonic acid and/or the sulphochloride and to recycle the phosgene, for example, together with sulphonic acid.

After the reaction with phosgene has ended, which can be recognised by the fact that the evolution of gas ceases, or using known analytical methods, highly volatile components are expelled by passing an inert gas in under a low vacuum.

Unreacted aromatic compound and, if appropriate, the solvent, is separated off, preferably by distillation, and, like the excess phosgene, re-used.

The sulphonic acid chloride which remains is either used as the crude product or, if necessary, purified by vacuum distillation or crystallisation. The process according to the invention can be carried out either discontinuously or continuously.

In a preferred preparation, for example of benzenesulphonyl chloride or diphenyl ether-disulphonyl chloride, it is possible, with respect to stage 1, (a) to initially introduce the aromatic compound, optionally together with the sulphonation auxiliaries, some or all of the latter being added, and to add the chlorosulphonic acid, if appropriate with the remainder of the sulphonation auxiliary at a rate depending on the rate of reaction, or (b) in a preferred procedure, to initially introduce the chlorosulphonic acid and if appropriate the sulphonation auxiliaries, in each case all or some of the compounds being added, and to add the aromatic compound, if appropriate together with the rest of the chlorosulphonic acid and the sulphonation auxiliaries, at a rate depending on the rate of reaction.

In the preparation of benzenesulphonyl chloride, stage 1 is preferably carried out at 20°–80° C., in particular at 40°–70° C.

Surprisingly, a decrease in the sulphone formation with a simultaneous increase in yield of benzenesulphonyl chloride is found for the entire reaction (stage 1 and stage 2) if the reaction in stage 1 is carried out in the presence of sulphonation auxiliaries at elevated temperature. On the other hand, the yield of benzenesulphonyl chloride falls at elevated temperature in the absence of sulphonation auxiliaries.

The hydrogen chloride obtained as a by-product is removed and can optionally be isolated. After the first reaction stage has ended, which can be recognised by the fact that the evolution of gas ends, the optionally reacted aromatic compound and, if appropriate, the solvent, can be distilled off.

The remaining reaction product from the first stage is now introduced into a mixture of phosgene and, preferably a N,N-dialkylcarboxylic acid amide, or into the suspension of the adduct of these components in liquid phosgene, preferably at 40° to 70° C., in a manner such that phosgene, or an adduct of phosgene and the N,N-dialkylcarboxylic acid amide, is always present in excess in the reaction mixture of the second reaction stage thus formed. In this stage also, the hydrogen chloride liberated is removed and optionally isolated. After the reaction has ended, the excess phosgene can be recovered in a manner which is in itself known. The reaction mixture which remains is worked up, for example by fractional distillation under reduced pressure, preferably in the range from 0.1 to 10 mbars.

In contrast to the individual reaction steps, which are in themselves known, very pure sulphonic acid chlorides are obtained in high yields, relative both to the aromatic compound employed and to the chlorosulphonic acid used, by the process according to the invention.

Compared with the known process, a particular industrial and ecological advantage of the process according to the invention is also, especially, that it is possible to work up the reaction mixture by distillation.

The excess phosgene, if appropriate the solvent and any unreacted chlorosulphonic acid or unreacted aromatic compound, can be distilled off, preferably under reduced pressure up to about 10 mm Hg, and re-used. One can then obtain the sulphonic acid chloride in high purity from the residue, by crystallisation or by distillation under reduced pressure, preferably under 0.1 to 15 mm Hg and in particular under 0.5 to 10 mm Hg.

Recovery of product by distillation, which is enabled by the process according to the invention, makes expensive working up with water unnecessary and avoids the dilute acid unavoidably obtained.

EXAMPLE 1 TO 6

116.5 g (1.0 mol) of chlorosulphonic acid and 5.0 g (0.068 mol) of dimethylformamide are initially introduced into the reaction flask and 78.1 g (1.0 mol) of benzene are added dropwise to this mixture in the course of four hours. The reaction mixture is stirred until the evolution of gas has ended and unreacted benzene is then distilled off under a waterpump vacuum.

15 g (0.2 mol) of dimethylformamide are initially introduced into a second flask and about 15 ml of condensed phosgene are added. The reaction mixture, which has been freed from benzene, from the first stage is then added dropwise to the second reaction flask in the course of four hours. Phosgene is simultaneously metered in such that it is always present in the reaction mixture of the second stage in excess, relative to the benzenesulphonic acid, which can be recognised by the vigorous reflux. After the dropwise addition has ended, the mixture is stirred until the evolution of gas has ended. Phosgene residues and other volatile constituents of the reaction mixture are stripped off under a waterpump vacuum. The residue is then subjected to fractional distillation in an oilpump vacuum over a mirrored column (3 cm × 30 cm).

Further details for the procedure and the results of the experiments can be seen from the table which follows. The total yields are relative to the conversion by sulphonation, calculated from the amount of benzene recovered.

Table for Examples 1 to 6

| Example | Sulphonation temperature (°C.) | Conversion by sulphonation (%) | Phosgenation temperature (°C.) | Product fractions | | Total yield |
| --- | --- | --- | --- | --- | --- | --- |
| 1 | 20 | 80.5 | 20 | I | 121.1 g (98.7% pure) | 88.6% |
|   |    |      |    | II | 14.8 g (43.5% pure) |       |
| 2 | 20 | 82.7 | 60 | I | 122.8 g (98.6% pure) | 86.8% |
|   |    |      |    | II | 11.6 g (49.1% pure) |       |
| 3 | 40 | 77.7 | 40 | I | 116.2 g (99.4% pure) | 88.2% |
|   |    |      |    | II | 8.7 g (62.9% pure) |       |
| 4 | 40 | 77.4 | 60 |   | 127.7 g (95.4% pure) | 92.7% |
| 5 | 60 | 76.7 | 60 | I | 123.0 g (99.0% pure) | 92.4% |
|   |    |      |    | II | 15.0 g (22.9% pure) |       |
| 6 | 80 | 83.7 | 60 | I | 123.6 g (98.9% pure) | 86.2% |
|   |    |      |    | II | 8.3 g (62.1% pure) |       |

EXAMPLE 7

Example 7 was carried out analogously to Example 1 to 6, using the same batch size. Phosphoric acid (5 g) was used as the sulphonation auxiliary instead of dimethylformamide. The first stage (sulphonation) was carried out at 70° C. and the second stage (phosgenation) was carried out at 60° C.

After distillation, 126.1 g of main runnings (99.5% pure) and 5.3 g of last runnings (81.9% pure) were obtained.

The total yield is 86.4% of theory, relative to benzene reacted (conversion by sulphonation: 85.1%).

EXAMPLE 8 TO 10

Examples 8 to 10 were carried out analogously to Example 4, but the amount of dimethylformamide (DMF) used as the sulphonation additive was varied. Details can be seen from the table which follows:

Table for Examples 8 to 10

| Example | Amount employed | DMF added | Conversion by sulphonation | Product fractions | | Total yield |
| --- | --- | --- | --- | --- | --- | --- |
| 8 | 1.0 mol | 1.5 g (0.02 mol) | 72.5% | I | 112 g (98.3% pure) | 89.0% |
|   |         |                  |       | II | 10 g (38.5% pure) |       |
| 9 | "       | 3.7 g (0.05 mol) | 79.5% | I | 123.5 g (99.1% pure) | 91.3% |
|   |         |                  |       | II | 8.5 g (68.6% pure) |       |
| 10 | "      | 5.9 g (0.08 mol) | 77.0% | I | 119.5 g (98.4% pure) | 90.4% |
|    |        |                  |       | II | 11 g (49.3% pure) |       |

EXAMPLE 11

Example 11 was carried out analogously to Example 9, with the deviation that chlorosulphonic acid was used in excess (122.5 g; 1.05 mols). After distillation, 128 g of main runnings (99.2% pure) and 5.5 g of last runnings (71.8% pure) were obtained.

The total yield is 90.8% of theory, relative to benzene reacted (conversion by sulphonation: 81.6%).

EXAMPLE 12

Example 12 was carried out analogously to Example 1 to 6, but phosphoric acid (3 g) was used as the sulphonation auxiliary; the sulphonation was carried out at 40° C. and the phosgenation was carried out at 60° C.

After distillation, 125 g of 99.3% pure benzenesulphonyl chloride were obtained.

The total yield is 91.4% theory, relative to benzene reacted (conversion by sulphonation: 77.0%).

What is claimed is:

1. In a process for the preparation of a sulphonic acid chloride of the formula

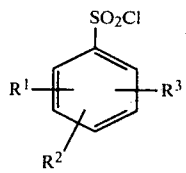

wherein $R^1$, $R^2$ and $R^3$ are identical or different and denote hydrogen, a lower alkyl radical or a cycloalkyl radical, halogen, aryl, aralkyl, aryl ether or a radical —$SO_2Cl$, —$SO_2$-aryl

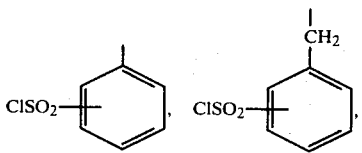

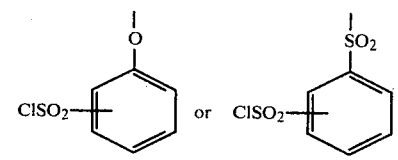

or wherein adjacent radicals $R^1$ and $R^2$ are linked to form a cycloaliphatic or aromatic carbocyclic ring which is optionally substituted by a sulphonic acid chloride group, contacting an aromatic compound of the formula

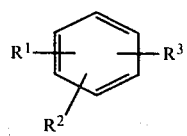

wherein $R^1$, $R^2$ and $R^3$ have the above-described meanings with chlorosulphonic acid and phosgene, the improvement which comprises contacting said aromatic compound with chlorosulphonic acid initially and thereafter contacting the resultant reaction product with phosgene in the presence of a catalyst.

2. A process according to claim 1 wherein the initial reaction of the aromatic compound with chlorosulphonic acid is carried out in the absence of phosgene.

3. A process according to claim 1 wherein the aromatic compound and chlorosulphonic acid are present in an approximately stoichiometric amounts with respect to one another.

4. A process according to claim 3 wherein the aromatic compound and chlorosulphonic acid are employed in a stoichiometric ratio of 1:1.

5. A process according to claim 1 wherein the chlorosulphonic acid is employed in an excess of up to 20 mol percent relative to the aromatic compound.

6. A process according to claim 1 wherein the reaction mixture obtained from the reaction of the aromatic compound with chlorosulphonic acid in the first process stage is reacted with phosgene in a second process stage in a manner such that phosgene is present in the reaction mixture of the second process stage in excess, relative to the reaction product from the first process stage.

7. A process according to claim 1 wherein $R^1$, $R^2$ and $R^3$ are independently lower alkyl radicals having between 1 and 6 carbon atoms, cycloalkyl radicals having between 5 and 6 carboxylic carbon atoms, halogens, phenyl aralkyl radicals of 6 to 18 carbon atoms where the aliphatic part contains 1 to 6 carbon atoms and the aromatic part is phenyl, a phenoxy radical or $R^1$ and $R^2$ taken together form a fused ring selected from the group consisting of an indane ring, a tetralin ring and a naphthaline ring.

8. In a process for the preparation of a sulfonic acid chloride of the formula

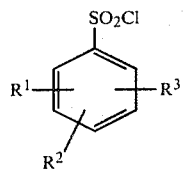

wherein $R^1$, $R^2$ and $R^3$ are identical or different and denote hydrogen, a lower alkyl radical or a cycloalkyl radical, halogen, aryl, aralkyl, aryl ether or a radical —SO$_2$Cl,—SO$_2$-aryl

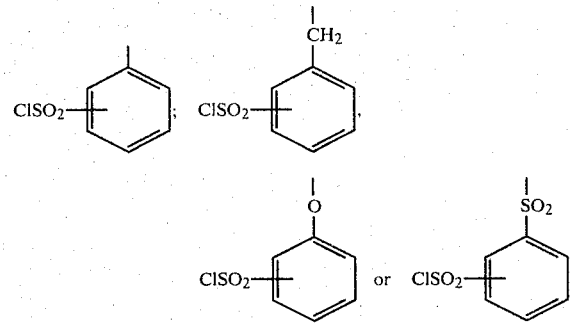

or wherein adjacent radicals $R^1$ and $R^2$ are linked to form a cycloaliphatic or aromatic carbocyclic ring which is optionally substituted by a sulphonic acid chloride group, contacting an aromatic compound of the formula

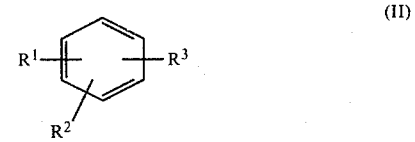

wherein $R^1$, $R^2$ and $R^3$ have the above-described meanings with chlorosulphonic acid and phosgene, the improvement which comprises contacting approximately stoichiometric amounts of said aromatic compound with chlorosulphonic acid initially and thereafter contacting the resultant reaction product directly without isolating the intermediate products with phosgene in the presence of a catalyst.

9. A process according to claim 8 wherein the chlorosulphonic acid is employed in an excess of up to 20 mole percent relative to said aromatic compound.

10. A process according to claim 9 wherein the initial reaction of the aromatic with chlorosulphonic acid is carried out in the absence of phosgene.

11. A process according to claim 10 wherein the aromatic compound with chlorosulphonic acid are present in an approximately stoichiometric amount with respect to one another.

12. A process according to claim 11 wherein the aromatic compound and chlorosulphonic acid are employed in a stoichiometric ratio of 1:1 to 1:1.2

13. A process according to claim 11 wherein the catalyst employed for the reaction of phosgene is dimethylformamide and the same is present in an amount up to 10 mol percent.

14. A process according to claim 13 wherein said dimethylformamide is present in an amount of up to 8 mol percent.

15. A process according to claim 14 wherein said dimethylformamide is present in an amount of up to 5 mol percent.

16. A process according to claim 11 wherein said phosgene is added to a reaction mixture comprising aromatic sulphonic acid in admixture with catalyst.

* * * * *